United States Patent [19]

Said et al.

[11] 4,016,258

[45] Apr. 5, 1977

[54] VASOACTIVE INTESTINAL PEPTIDE FROM FOWL

[76] Inventors: Sami I. Said, 5323 Harry Hines Blvd., Dallas, Tex. 75235; Viktor Mutt; Ann Nilsson, both of Medecinska Nobelinstitutet, Stockholm, Sweden

[22] Filed: Aug. 5, 1975

[21] Appl. No.: 602,102

[52] U.S. Cl. .......................... 424/177; 260/112.5 R
[51] Int. Cl.² ................ A61K 37/00; C07C 103/52
[58] Field of Search .............. 424/177; 260/112.5 R

[56] References Cited

UNITED STATES PATENTS

| 3,879,371 | 4/1975 | Said et al. | 260/112.5 R |
| 3,880,826 | 4/1975 | Said et al. | 260/112.5 R |

Primary Examiner—Lewis Gotts
Assistant Examiner—Reginald J. Suyat
Attorney, Agent, or Firm—Lowe, King, Price & Markva

[57] ABSTRACT

A polypeptide having important biological activity including systemic vasodilation, hypotension, increased cardiac output and bronchodilation is isolated from intestines of chickens. The isolation procedure for purification includes extraction, ion-exchange chromatography, gel chromatography and countercurrent distribution separation. The polypeptide has the general amino acid structure:

His-Ser-Asp-Ala-Val-Phe-Thr-Asp-Asn-Tyr-Ser-Arg-Phe-Arg-Lys-Gln-Met-Ala-Val-Lys-Lys-Tyr-Leu-Asn-Ser-Val-Leu-Thr-NH₂. Therapeutic biological actions may be produced in animals and humans by administration of 0.02–10 µg of the peptide per kg of body weight.

10 Claims, 3 Drawing Figures

CHROMATOGRAPHY ON SEPHADEX G-25
ABSORBANCE AT 280 nm

CHROMATOGRAPHY ON CM-CELLULOSE
ABSORBANCE AT 280 nm

COUNTER-CURRENT DISTRIBUTION
ABSORBANCE AT 215 nm

VASOACTIVE INTESTINAL PEPTIDE FROM FOWL

The invention described herein was made in the course of work under a grant or award from the Department of Health, Education and Welfare.

BACKGROUND OF THE INVENTION

1. Field of the Invention

This invention relates generally to a new polypeptide, its method of isolation, biological actions of the peptide, and its therapeutic usefulness. More particularly, the present invention relates to a new polypeptide isolated from the intestines of chickens or other fowl by means of novel purification procedures and to the wide-range of activity of the polypeptide which affect cardiovascular, respiratory and metabolic functions.

2. Description of the Prior Art

It is well-known that polypeptide hormones regulate many physiologic functions and mediate certain pathological responses. While numerous compounds have been known to possess a vasodilator effect, many possess this effect only to a relatively slight degree or for a very short time. Medical science has, therefore, sought materials exhibiting a more potent or sustained vasodilator effect which would be more useful therapeutic agents.

In earlier filed U.S. Pat. Applications Ser. No. 181,444, filed Sept. 17, 1971, now U.S. Pat. No. 3,879,371, and Ser. No. 417,605, filed Nov. 20, 1973, now U.S. Pat. No. 3,880,826, there is disclosed a vasoactive peptide and its method of isolation from the upper intestinal wall of porcine. The porcine vasoactive intestinal peptide was identified as an octacosapeptide of specific sequence which exhibited biological activity in the areas of systemic vasodilation, hypotension, increased cardiac output, respiratory stimulation and hyperglycemia. A report on this peptide and its method of isolation may be found in the literature in Science, 169, 1217–1218 (1970). Another publication of interest to the porcine vasoactive peptide may be found in Eur. J. Biochem., 42, (1974).

The present invention is concerned with a vasoactive octacosapeptide which has been isolated from the intestines of chickens and other fowl which is related to but distinctly different from the porcine peptide in structural sequence and biological activity.

SUMMARY OF THE INVENTION

It is accordingly a main object of the present invention to provide a new polypeptide exhibiting important biological actions.

It is a further object of the present invention to provide a new polypeptide exhibiting activity as a bronchodilator, systemic vasodilator, hypotensive and cardiac output increaser.

A still further object of the invention is the provision of separating techniques for isolating the polypeptide from intestines of chicken and other fowl through the use of chromatography and other separation procedures.

This invention also has as an object the provision of a new polypeptide having an amino acid structure which exhibits unexpected biological activity.

A further object of the invention is the provision of therapeutic compositions of matter containing the new polypeptide.

A further object of the present invention is a provision of a method of treating humans and animals by administration of the new polypeptide.

These and other objects of the present invention will become apparent as the description thereof proceeds.

In satisfaction of the foregoing objects and advantages there is provided by this invention a new and pure vasoactive intestinal peptide having biological activities which has the composition:
His-Ser-Asp-Ala-Val-Phe-Thr-Asp-Asn-Tyr-Ser-Arg-Phe-Arg-Lys-Gln-Met-Ala-Val-Lys-Lys-Tyr-Leu-Asn-Ser-Val-Leu-Thr-$NH_2$, said peptide being isolated from the intestines of chickens and other fowl by a process including the steps of obtaining chicken or other fowl intestines in the minced and frozen state, freed of pancreatic tissue, extracting with acetic acid, adsorbing on alginic acid, precipitating from an acid eluate, subjecting to ion-exchange chromatography, collecting fractions therefrom containing the peptide, extracting with an alcohol, subjecting to gel chromatography, collecting fractions, and subjecting to a countercurrent distribution separation and collecting the purified peptide. There are also provided therapeutic compositions of matter containing the peptide and use of the therapeutic compositions to produce biological actions in humans by administration thereof.

BRIEF DESCRIPTION OF THE DRAWING

Reference is now made to the drawings accompanying this application wherein.

DESCRIPTION OF PREFERRED EMBODIMENTS

Figures 1, 2, 3:
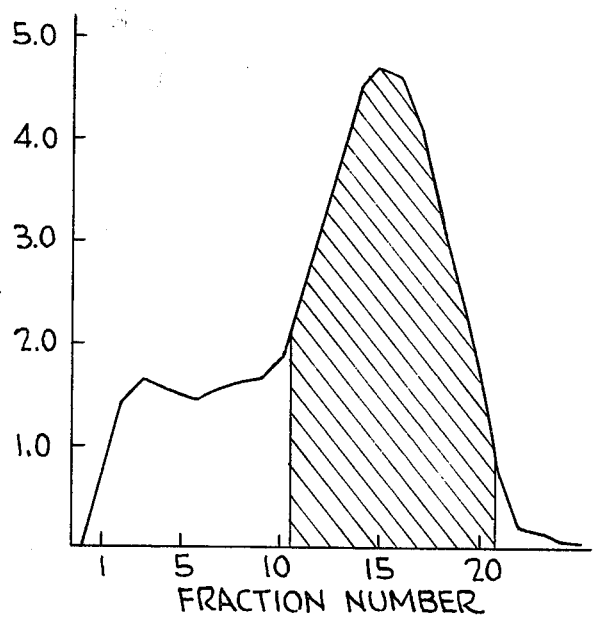
FIG. 1 represents a graph of the active fraction obtained from chromatography on Sephadex G-25.
FIG. 2 represents a graph of the active fractions obtained from chromatography on CM-cellulose.
FIG. 3 represents a graph of the pure product fraction obtained from countercurrent distribution.

The present invention is concerned with the isolation, purification, identification and biological uses of a new vasoactive intestinal octacosapeptide which is the first intestinal hormone to be isolated from the chicken or other fowl and which has been found to be potent in a number of biological areas. The vasoactive peptide of this invention has the following composition:
His-Ser-Asp-Ala-Val-Phe-Thr-Asp-Asn-Tyr-Ser-Arg-Phe-Arg-Lys-Gln-Met-Ala-Val-Lys-Lys-Tyr-Leu-Asn-Ser-Val-Leu-Thr-$NH_2$.

This polypeptide is illustrated herein with reference to the product isolated from chicken intestines.

This chicken vasoactive peptide is characterized by an N-terminal histidine residue which is like the porcine vasoactive peptide referred to above, secretin and glucagon. The peptide also has a residue of threonine amide constituting its C-terminus as compared to asparagine amide in the C-terminus of the porcine peptide.

In the above sequence of the peptide of this invention the amino acid components are identified by abbreviations for convenience. These abbreviations are as follows:

| Amino Acid | Abbreviated Designation |
|---|---|
| L-methionine | met |
| L-arginine | arg |
| L-alanine | ala |
| L-aspartic acid | asp |
| L-histidine | his |

-continued

| Amino Acid | Abbreviated Designation |
|---|---|
| L-lysine | lys |
| L-leucine | leu |
| L-phenylalanine | phe |
| L-asparagine | asn |
| L-serine | ser |
| L-tyrosine | tyr |
| L-threonine | thr |
| L-valine | val |
| L-glutamine | gln |

The structure of the polypeptide of this invention was determined by initially subjecting to quantitative amino acid analyses by the method of Spackman et al. (Anal. Chem 30, 1190–1206, 1958). The results from this initial determination provided the results shown in the following Table I as follows:

TABLE I

Amino acid composition of hydrolyzed chicken vasoactive intestinal peptide. Hydrolysis at 109° C. for 22 hours with 1 $\mu l/\mu g$ of 6 M HCl containing 0.5 o/oo mercaptoethanol.

| Amino Acid | Amount in peptide sample 240 $\mu g$ | 19 $\mu g$ nmol | Probable number of residues in peptides |
|---|---|---|---|
| Alanine | 110 | 8.9 | 2 |
| Arginine | 112 | 11.5 | 2 |
| Aspartic acid | 217 | 16.9 | 4 |
| Glutamic acid | 61 | 5.1 | 1 |
| Glycine | 7 | 0.6 | 0 |
| Histidine | 53 | 5.5 | 1 |
| Isoleucine | 0 | 0 | 0 |
| Leucine | 111 | 9.9 | 2 |
| Lysine | 155 | 16.7 | 3 |
| Methionine | 50 | present | 1 |
| Phenylalanine | 102 | 10.3 | 2 |
| Serine | 168 | 10.8 | 3 |
| Threonine | 110 | 8.7 | 2 |
| Tyrosine | 102 | 10.1 | 2 |
| Valine | 142 | 13.7 | 3 |
| | | Total | 28 |

In further identification, it was found that tryptophan and cystine/cysteine were absent as shown by the Voisnet-Rhode dimethylaminobenzaldehyde reaction (Anal. Chem. 21, 1249–1266, 1949), and by analysis of material oxidized with performic acid according to Moore, (Biol. Chem. 238, 235–237, 1963), respectively. In order to determine the C-terminal amino acid, chymotrypsin digestion was conducted for 4 hours at 24° C. in 1% $NH_4HCO_3$ using 0.04 mg/ml enzyme and 2 mg/ml peptide. One-half the quantity of the enzyme was added to the substrate at the beginning of the degradation and the other half after two hours. In parallel with this, the porcine vasoactive octacosapeptide mentioned above was treated by exactly the same procedure. The digests were lyophilized, redissolved in half the original volume of water and heated for 6 minutes at 100° C. They were then lyophilized in 0.2 M acetic acid and submitted to high voltage paper electrophoresis at a pH of 6.4. It was found that whereas, as expected, asparagine amide could be clearly identified among the chymotryptic degradation products of the porcine polypeptide, no trace of this group could be seen among the fragments from the chicken material. Instead, there was a fragment with higher cathodic mobility giving a canary yellow color with the cadmium-nin-hydrin reagent of Barrollier et al. (Biochemistry, 4, 2358–2362, 1965). This yellow color was indicative of either a glycyl or threonyl peptide. Since the amino acid analysis had shown that the chicken, like the porcine material, lacked glycine, the chymotryptic degradation products of the chicken polypeptide were run in parallel and mixed with threonyl amide. The results confirmed that the C-terminal amino acid in chicken vasoactive octacosapeptide is threonine amide.

The determination of the final structure or sequence of the polypeptide was carried out by pancreatic kallikrein cleavage.

CLEAVAGE OF THE PEPTIDE WITH KALLIKREIN AND SEPARATION OF THE FRAGMENTS

In this determination, four mgs. of the octacosapeptide isolated as described herein were degraded with kallikrein. Electrophoresis of an aliquot at pH 6.4 showed that it had been split into one neutral and one basic fragment. The bulk of the degraded material was dissolved to a 1% solution in 0.02 M $NH_4HCO_3$ adjusted to pH 6.5 with $CO_2$ and followed by this buffer, passed through a column (0.6 × 15 cm) of carboxymethyl-cellulose, CMC, (Whatman CM-22) which had been equilibrated with the same buffer. A fraction of 5 ml. was collected whereupon the buffer was changed to 0.04 M $NH_4HCO_3$ and a second fraction of 5 ml. collected. The buffer was changed to 0.08 M, 0.16 M, and 0.4 M $NH_4HCO_3$ and one fraction of 5 ml collected from each. The fractions were lyophilized. The first fraction contained the neutral and the fourth fraction the basic fragment. The neutral fragment, which gave a positive Pauly reaction was denominated CV-KN. It weighed 1.4 mgs. The basic fragment gave a negative Pauly reaction and was denominated CV-KC. It weighed 1.1 mgs.

AMINO ACID SEQUENCE OF CV-KN

Fragmentation of CV-KN with Trypsin. On degradation of 1.4 mg. CV-KN with trypsin, two fragments were again formed: one with cathodic electrophoretic mobility at pH 6.4 and one with anodic mobility and a positive Pauly reaction. The peptide mixture was applied to a CMC column (0.6 × 11.5 cm) in 0.02 M $NH_4HCO_3$. Two fractions of 4 ml. were collected whereupon the eluant was changed to 0.2 M $NH_4HCO_3$ and two more fractions of 4 ml. each collected. The first fraction contained the Pauly positive fragment which was denominated CV-KN-TrN. It weighed about one mg. The third fraction contained the Pauly negative one which was denominated CV-KN-TrC. Qualitative amino acid analysis of hydrolyzed samples of it contained only phenylalanine and arginine.

Fragmentation of CV-KN-TrN with Chymotrypsin. CV-KN-TrN was degraded with chymotrypsin into three fragements: One with cathodic mobility at pH 6.4 and two with anodic mobilities. The fragment with cathodic mobility gave a positive Sakaguchi and a negative Pauly reaction. With the cadmium-ninhydrin reagent it gave an orange-red color. It was denominated CV-KN-TrN-ChtC. The fragment with the lower anodic mobility gave a color in the Pauly reaction like that given by histidine. It was Sakaguchi negative and denominated CV-KN-TrN-ChtN. The fragment with higher anodic mobility gave a color in the Pauly reaction like that given by tryrosine and was Sakaguchi negative. It gave a brilliant yellow color with the ninhydrin-cadmium reagent and was denominated CV-KN-TrN-Chti. The three fragments were separated on a column (0.6 × 23 cm) of SE-Sephadex similarly to the separation of the three chymotryptic fragments of the N-terminal tryptic dodecapeptides of porcine vasoactive intestinal peptide and secretin.

Evidence for the Sequence of CV-KN. Determination of N-terminal amino acid residues, qualitative amino acid analysis of acid or enzymatic (aminopeptidase M) hydrolyzates and the specificity of the fragmentation agents used gave, when correlated with the known quantitative amino acid composition of CV-KN, the following information about these subfragments of the tetradecapeptide:

CV-KN-TrN-ChtN was His(Ala,Asp,Ser,Val)Phe
CV-KN-TrN-Chti was Thr(Asn,Asp)Tyr
CV-KN-TrN-ChtC was Ser-Arg
CV-KN-TrC was Phe-Arg This suggested that CV-KN-TrN-ChtN and CV-Kn-TrN-Chti might be identical with the corresponding porcine peptides. They were therefore subjected to amino acid sequence determination exactly as described for the latter and the suspected identities were indeed confirmed. These results show that the 14 first amino acids of the chicken octacosapeptide are in the sequence: His-Ser-Asp-Ala-Val-Phe-Thr-Asp-Asn-Tyr-Ser-Arg-Phe-Arg.

AMINO ACID SEQUENCE OF CV-KC

Fragmentation with Cyanogen Bromide. CV-KC, 1.1 mgs., was treated with cyanogen bromide and passed through a DEAE-Sephadex column (0.6 × 105 cm) in 0.2 M acetic acid. The degraded chloride-free lyophilized material was dissolved in 1 ml. M acetic acid and chromatographed in this solvent on a column of Sephadex G-25 (0.6 × 105 cm). Flow rate 0.5 ml/4 min. Sixty fractions were collected. All fractions were lyophilized and then reconstituted in 50 $\mu$l. of water. Aliquots of 1:$\mu$l from each fraction were applied to a strip of Whatman 42 filter paper and the strip was, after drying, drawn through the cadmium-ninhydrin solution. The material from fractions 23–30 and 32–35 were ninhydrin positive. An acid hydrolyzate of an aliquot of the combined fractions 23–30 showed that the material contained alanine, aspartic acid, leucine, lysine, threonine, tyrosine, serine and valine. After lyophilization the material was denominated CV-KC-CNBr-C. A similar hydrolyzate of fraction 32–35 contained homoserine, glutamic acid and lysine. It was denominated CV-KC-CNBr-N.

The lysine was shown to be N-terminal, and, on electrophoretic evidence, glutamine, rather than glutamic acid, to be present in the intact peptide.

Degradation of CV-KC-CNBrC with Chymotrypsin. When CV-KC-CNBrC was degraded with cymotrypsin three fragments, one neutral and two basic, were formed as shown by paper electrophoresis at pH 6.4. The basic fragment with highest electrophoretic mobility gave a canary yellow color with the cadmium-ninhydrin reagent similar to that given by peptides with N-terminal threonine. Its electrophoretic mobility was identical with that of threonine amide, shown earlier to be C-terminal in chicken VIP. The other two fragments gave the usual reddish color. The separation of the three fragments on a CMC column (0.6 × 25 cm) with 0.02 M NH$_4$HCO$_3$ adjusted to pH 6.5 with CO$_2$, and then 0.2 M NH$_4$HCO$_3$ followed closely the similar separation of the corresponding fragments from the porcine material. Fifty-five fractions of 1 ml. each were collected. The change of buffer was made after the 40th fraction. On paper electrophoresis of aliquots it was found that the material from fractions 7–11 constituted the neutral chymotryptic fragment of CV-KC-CNBrC. It was found to have N-terminal leucine and was denominated CV-KC-CNBrC-Chti. The material from fractions 19–23 was the basic fragment with highest electrophoretic mobility and the yellow color with the ninhydrin reagent, and was denominated CV-KC-CNBrC-ChtC. The material from fractions 47–50 was the basic fragment with lower electrophoretic mobility and "ordinary" reddish color with the ninhydrin reagent. It was found like CV-KC-CNBrC itself to have N-terminal alanine and was denominated CV-KC-CNBrC-ChtN.

THE AMINO ACID COMPOSITIONS AND SEQUENCE OF THE THREE CHYMOTRYPTIC FRAGMENTS

Paper chromatography of an acid hydrolyzate showed that CV-KC-CNBrC-ChtN contained the same amino acids as the corresponding peptide from the porcine octacosapeptide, suggesting that their sequence also might be identical. This was shown to be so by subjecting the chicken peptide to the same treatment as had been used to elucidate the sequence of the porcine peptide, i.e., showing that its N-terminal amino acid was alanine and splitting it by trypsin into the two fragments which were identified as Ala-Val-Lys and Lys-Tyr.

CV-KC-CNBrC-Chti was found to have N-terminal leucine, like the corresponding porcine peptide, but it differed from the latter by containing valine and no isoleucine. It was subjected to the same treatment that had been used for elucidating the sequence of the corresponding porcine peptides. Thermolysin split it into two fragments which were isolated by paper chromatography in the Waley-Watson system, and identified as Leu(Asn,Ser) and Val-Leu. Proteinase K split it into two main fragments identified as, Leu-Asn and Ser-Val-Leu, and besides, to a smaller extent, into the same fragments as given by thermolysin. The combined results with these two enzymes established the sequence of the neutral chymotryptic pentapeptide as Leu-Asn-Ser-Val-Leu. An acid hydrolyzate of the basic fragment from fractions 19–23 contained threonine only. It had already been determined that the C-terminus of the chicken vasoactive octacosapeptide was threonine amide.

These results gave the following information about the subfractions of the C-terminal tetradecapeptide CV-KC:

CV-KC-CNBrN was Lys-Gln-Homoserine
CV-KC-CNBrC-ChtN was Ala-Val-Lys-Lys-Tyr
CV-KC-CNVrC-Chti was Leu-Asn-Ser-Val-Leu
CV-KC-CNBrC-ChtC was ThrNH$_2$ The sequence of the chicken vasoactive intestinal octacosapeptide was consequently determined to be as follows:
His-Ser-Asp-Ala-Val-Phe-Thr-Asp-Asn-Tyr-Ser-Arg-Phe-Arg-Lys-Gln-Met-Ala-Val-Lys-Lys-Tyr-Leu-Asn-Ser-Val-Leu-ThrNH$_2$ This differs from the corresponding porcine sequence by the replacement of Thr-11 by Ser-11, of Leu-13 by Phe-13, of Ile 26 by Val 26 and by the C-terminal residue of asparagine amide by a residue of threonine amide.

This vasoactive intestinal octacosapeptide is the first intestinal hormone to be isolated from the chicken and indeed from any species other than porcine. Gastrin has been isolated in chemically pure form from several mammalian species, but not from non-mammalian species. Secretin has been isolated only from the hog or porcine. Pancreatic glucogen on the other hand has been isolated from several mammalian species as well as the turkey and duck. While no differences have been found in the amino acid sequences among the hitherto isolated mammalian glucagons, the avian hormones differ from the common mammalian variant by the replacement of one amino acid residue, asparagine-28, by serine (turkey), or by two residues, asparagine-28 by serine, and serine-16 by threonine, (duck). As in the porcine vasoactive peptide, secretin and glucagon, the N-terminal amino acid of the chicken vasoactive octacosapeptide is histidine. The C-Terminus is threonime amide. The polypeptide has been isolated and purified to a high degree over its existence in the chicken.

The vasoactive octacosapeptide of this invention has a wide variety of biological actions and is effective on the cardiovascular system, that is, in systemic vasodilation and reducing blood pressure. Further, the peptide exhibits smooth muscle relaxant activity. The polypeptide of this invention has been compared with the porcine vasoactive intestinal peptide referred to above with respect to the biological activities and found that in the comparison, the chicken peptide is a relatively more potent relaxant of guinea pig trachea than any other smooth muscles tested. Also, the hypotensive effect in dogs of the chicken peptide is less marked and shorter lasting than the porcine peptide.

The most notable feature of the reaction of the chicken peptide is the relatively pronounced and prolonged relaxation of the trachea. Thus, in comparing the chicken peptide with the porcine peptide in doses eliciting equal relaxation of the stomach, the relaxation of the trachea was many times greater with the chicken peptide. The chicken peptide is also particularly useful as a bronchodilator and for this purpose it may be administered by injection or by the aerosol method. The latter approach minimizes its effects on blood pressure and on other systemic effects and concentrates its action on the air passages.

As indicated above, the polypeptide of this invention was isolated from the intestines of chicken by a series of manipulative steps carried to sufficient purification for determination of structure and activity. The chicken pancreas is composed of three lobes that occupy the space between the limbs of the duodenum. Three secretory ducts pass to the distal end of the duodenal loop and open on a common papilla with the bile duct. From broilers of the variety Hybro ranging from 1000–1100 grams in weight, the duodenum and uppermost part of the jejunun, together with about 15 centimeters, were removed as soon as possible after killing the chickens. The intestines were freed of pancreatic tissue, rinsed with water and immersed for 10 minutes in boiling eater. After mincing, the material was stored at −20° C. At this stage, the concentrate material was in condition for treatment for recovery of the peptide.

In the early stages of the process of isolation, the material was treated as for the preparation of porcine secretin according to the procedure of Mutt, Ark. Kemi, 15, 69–74 (1959), until the second treatment with alginic acid. In general, the procedure of Mutt involves extraction of the minced material with acetic acid, adsorbing on alginic acid, elution with 0.2N HCl and precipitation or salting out with sodium chloride at the saturation point. The resulting precipitate is then filtered, washed and again adsorbed with alginic acid with elution by 0.2N HCl with stirring for 1 hour. After filtering, the active material is then again precipitated with sodium chloride at the saturation point and the precipitate collected on a suction filter and dried.

According to the present invention, it was discovered that the crude concentrate must first be subjected to gel chromatography followed by extraction with an alcohol, thereafter followed by separation by ion-exchange chromatography, and finally a countercurrent distribution separation.

According to the method of purification of this invention the resulting dried concentrate of peptide from the alginic acid treatment is subjected to a chromatographic separation in the presence of a gel such as a cross-linked dextran, e.g., Sephadex G-25, in a column which has been previously washed with acetic acid. This gel chromatography separation is utilized to separate the various polypeptide molecules in accordance with their size. The column may be Sephadex, which is a well-known cross-linked dextran frequently used for this purpose, or cellulose or a like gel filtration medium. The crude concentrate from the previous step is dissolved in an organic acid such as acetic acid. The concentraion of the acid is not critical but may vary from approximately 0.1M to 0.3M. The preferred organic acid is acetic acid. From this chromatographic step, fractions are collected beginning with the introduction of the popypeptide solution into the column. Fractions are then combined and saturated with sodium chloride and the material salted out and reprecipitated. Thereafter, this material is extracted with a lower alkyl alcohol of the formula R-OH where R is alkyl of 1 to 7 carbons, such as methanol, and an inert fraction removed by neutralization. The active material is then precipitated after acidification and dissolved in water. The resulting product is salted out or precipitated with sodium chloride.

In the next step, the intermediate product is dissolved in a buffered solution at a pH of 6–7 and subjected to ion-exchange chromatography.

The ion-exchange chromatography separation preferably utilizes carboxy methyl cellulose (CMC), though other ion-exchange media may be utilized. The buffer may be an alkali metal (Na, $NH_4$) carbonate or bicarbonate, phosphate or acid phosphate. The concentration of the buffer is not critical but preferably may vary between approximately 0.01 and 0.015M. The pH of the buffer solution should be between 6 and 7, preferably between 6.2 and 6.6. The solution was allowed to pass through the column with elution carried out by linear gradients. Fractions are obtained, combined and desalted on a cross-linked dextran column in 0.2M acid. After lyophilization, the material was recovered and subjected to the final purification step.

The final purification step comprises a countercurrent distribution separation. The systems preferred for conducting this step include an organic solvent, for example: alcohols such as methanol and 1-butanol and an aqueous solvent, preferably alkali metal salts of chlorides, bicarbonates, phosphates, etc; for example, sodium chloride, potassium phosphates and ammonium bicarbonate. At least a 20 tube separation system should be used, but also a several hundred tube system may be used, or even greater. The concentration of the aqueous solvent such as ammonium bicarbonate may vary from about 0.05M to 0.15M. Again, the concentrations are not critical. The separations are made in an inert atmosphere, e.g., under nitrogen or argon.

The collections are made on the basis of the optical densities of the homogenous tube contents as determined at 215 µg and 1-cm light path. After completion of the run, the two phases are coalesced by the addition of a lower alcohol such as ethanol and the absorbence determined to provide the active materials. The contents of the two phases were then combined and the pH brought to 2.5 to 2.7 with a mineral acid such as HCl and the polypeptides recovered by adsorbtion to aglinic acid, elution with 0.2M HCl and exchange of chloride for acetate followed by lyophilization.

BIOLOGICAL EFFECTS

The novel vasoactive peptide of this invention has been found to be useful in several important areas. These properties have been determined in two different systems:

1. Intact anesthetized dogs

The peptide was infused into one femoral artery, and the blood flow in that artery, as well as the aortic blood pressure, were continually measured. During the infusion of the peptide, blood pressure fell and blood flow increased, indicating peripheral vasodilation. The effects were relatively prolonged, lasting approximately 15 to 30 minutes with the infusion of 1–10 µg/minute, for one minute.

2. Isolated smooth-muscle organs

Four strips of smooth-muscle organs: rat stomach, guinea pig trachea, rat colon, and guinea pig gallbladder, were placed in series and superfused with warm physiological solution (Krebs), bubbled with 95% $O_2$ and 5% $CO_2$. The organ strips were attached to special transducers which measured their contraction or relaxation. Addition of chicken peptide to the physiological solution caused relaxation of stomach and trachea, except that the stomach strip often showed an initial brief contraction which was followed by relaxation. Effects on gallbladder were variable, and colon usually contracted.

Because of its characteristics, the polypeptide is useful in a number of important areas. Thus, it affects the cardiovascular system as it will affect peripheral (systemic) vasodilation, lowers blood pressure, and relaxes the bronchial smooth muscle. Also, the peptide exhibits excellent smooth muscle-relaxant activity.

A most notable feature of the actions of this compound was the relatively pronounced and prolonged relaxation of the trachea. On comparing chicken peptide with the porcine peptide, in doses eliciting equal relaxation of stomach, the relaxation of trachea was many times greater with the chicken peptide.

An important use of the peptide is in the area of bronchodilation as a bronchodilator. For this purpose the peptide may be given by injection or by aerosol. The latter approach would minimize its effects on blood pressure and other systemic effects, and concentrate its action on the air passages. An important advantage of the peptide with respect to lowering blood pressure and bronchodilation is that the lowering of blood pressure is of relatively short duration, e.g., when compared with the procine peptide. As all bronchodilators lower blood pressure, it is important that the hypotensive activity be as brief as possible. The peptide of the invention meets this requirement.

The potent vasodilator action of the peptide suggests usefullness in promoting peripheral blood flow in extremities, and in relieving pulmonary hypertension in disease states associated with constriction of pulmonary vessels and in the relief of coronary angina pectoris. Because of its hypotensive action, the polypeptide suggests usefulness as an additional tool in the management of systemic hypertension. The smooth-muscle relaxant properties of the polypeptide render it useful in the management of excessive contractions of certain organs such as gallbladder.

DOSAGE AND ADMINISTRATION

It is recommended that the dosage to humans or animals be by intravenous injection of 0.02–10 µg per kg of body weight for most biological conditions. When used as a bronchodilator and adminstered by the aerosol or oral route, a suitable dosage is 1 to 5 micrograms per kg. of body weight. The carrier may be any physiologically safe and unreactive solvent, many of which are well known in the art. Among those considered useful are the normal saline solutions, THAM solution, and others. The concentration of peptide in the carrier may vary widely, e.g., from 0.001 to 0.10 weight percent. For use as a bronchodilator, however, it is preferred that the peptide be adminstered by other methods such as by oral administration, by nasal spray, aerosol spray, or sublingually for coronary dilation.

EXAMPLE

In the following specific example, the alginic acid, Sephadex G-25 (fine) and carboxymethyl cellulose were obtained from the same commercial sources. Porcine, secretin and vasoactive intestinal octacosapeptide were the natural hormones prepared in the laboratory. Hydrochloric acid was of Aristar quality from BDH. Tosyl-lysyl-chloromethyl ketone treated chymotrypsin was from E. Merck (Darmstadt). L-aspartic acid diamide HCl hemihydrate was obtained from Cyclo Chemical and L-threonine amide from Fox Chemical Company, Los Angeles, California.

The acid catalyzed hydrolysis of the peptide was carried out for 22 hours at 109° C. in an atmosphere of argon using 6 M HCl containing 0.5% mercaptoethanol. Qualitative amino acid analyses were carried out either by two dimensional paper chromotgraphy or by cellulose thin-layer chromotgraphy.

A column of Sephadex G-25 (fine) with the dimensions 4 × 90 cm and carboxymethyl-cellulose column with the dimensions 0.9 × 16 cm were prepared and stored under 0.2 M acetic acid containing 3 o/oo tricresol R and 0.1 M NaOH respectively, until required for the chromotographic steps.

PRELIMINARY SEPARATION

The chicken pancreas is composed of three lobes that occupy the space between the limbs of the duodenum. Three secretory ducts pass to the distal end of the duodenal loop and open on a common papilla with the bile duct. From broilers of the variety Hybro ranging from 1000 to 1100 grams in weight, the duodenum and the uppermost part of jejunum, together about 15 cm, were removed as soon as possible after killing the chickens. The intestines were freed of pancreatic tissue, rinsed with water and immersed for ten minutes in boiling water. After mincing, the material was stored at −20°

C. It was then treated as for the preparation of porcine secretin by extraction with constant stirring overnight at room temperature with 200 liters of 0.5 N acetic acid. Two kg of Hyflo Super-Cel were then added to the extraction mixture, and the resulting suspension filtered through bags of linen cloth. It was stirred with 2 kg of alginic acid, which had previously been washed with water, 0.2 N HCl, and water again. The alginic acid containing the adsorbed peptide was allowed to sediment for a few hours. The supernatant was discarded, and the sediment transferred to suction filters, on which it was washed with 0.005 N HCl and then with 95% ethanol to remove the fats. The ethanol was either allowed to evaporate, or washed off with 0.005 N HCl. The peptide was eluted from the alginic acid with 20 liters of 0.2 N HCl under stirring for one hour. After filtering, the active material was precipitated from the eluate with sodium chloride at saturation. The precipitate was collected on a suction filter and sucked as dry as possible. From 100 kg intestines of about 20,000 chickens, approximately 40 grams of peptide concentrate (net weight) were obtained.

CHROMATOGRAPHY ON THE SEPHADEX G-25 (FINE) COLUMN

The column was washed with 0.2 M acetic acid until free of tricresol. A solution of 4 grams starting material in 40 ml. 0.2 M acetic acid was filtered through a Millipore filter of 0.45 $\mu$ porosity and allowed to sink into the column. Elution was carried out with 0.2 M acetic acid with a flow rate of 5 ml/minute. Fractions of 10 ml. each were collected, starting with the introduction of the polypeptide solution into the column. FIG. 1 shows the absorbance of 280 nm. Fractions 11–22 as illustrated by shading were combined and saturated with sodium chloride. The salted out material weighed 1.1 grams. After reprecipitation at pH 4.0 it weighed 0.93 gram.

EXTRACTION WITH METHANOL

Salted out material from the Sephadex G-25 column, weighing 3.8 grams was extracted with methanol, an inert fraction removed by neutralization of the extract and the active material, precipitated with ether after acidification with HCl, and dissolved in water. The solution was saturated with sodium chloride. The salted out material weighed 101 mg. The methanol-insoluble fraction weighed 1.6 gram and contained cholecystokinin-pancreozymin activity.

CHROMATOGRAPHY ON CARBOXYMETHYL-CELLULOSE

Prior to chromatography, CMC-column was equilibrated with 75 ml. of 0.0225 M sodium phosphate buffer of pH 6.4 to 75 ml. of the buffer 0.3 M in NaCl. The column was 0.9 × 16 cm. 100 mg of the methanol extracted material was dissolved in 8 ml. of the buffer and adjusted to pH 6.4 with 0.03 M NaOH. The solution was allowed to sink into the column and elution was carried out in a linear gradient from 75 ml. of the starting buffer to 75 ml. of this buffer made 0.3 M in NaCl. Fractions at a flow rate of 1.5 ml/2.5 minutes were collected. FIG. 2 shows the absorbance at 280 nm and the fractions collected are represented by shading.

When tested in the cat it was found that the ability to stimulate pancreatic secretion was confined mainly to two areas of the chromatogram, fractions 33 to 39 and fractions 62 to 69. The latter showed also a strong vasoactivity when tested in the dog. Fractions 33 and 39 were combined and desalted on a Sephadex G-25 (coarse) column (1.5 × 90 cm) in 0.2 M acetic acid. After lyophilization the material weighed 4 mg. Fractions 62 to 69, when treated in the same manner yielded 7 mgs. The pancreas stimulating i.e., secretin-like material prepared in this way contained approximately 50 clinical units per mg.

The pancreas stimulating and vasoactive material (from fractions 62 to 69) were then subjected to countercurrent distribution.

COUNTERCURRENT DISTRIBUTION

Sixty mg of the material obtained as described in the preceding section was subjected to countercurrent distribution. The apparatus (from H. O. Post, Inc., Middle Village, New York, U.S.A.) and the use of an inert nitrogen atmosphere were the same as used for secretin and the porcine vasoactive peptide. Distribution was through 200 transfers during 70 hours in a nitrogen atmosphere. The phase system was n-butanol-0.1 M $NH_4HCO_3$ and the phase volume was 10 ml. After completion of the run, the two phases were made to coalesce by the addition of 3 ml. per tube of ethanol. The absorbance of the homogenous tube contents was determined at 215 nm and 1-cm light path. The light absorbance was measured on combined phases obtained by the addition of 3 ml. of ethanol to each tube. The contents of tubes 65–100 were combined and dissolved in 20 volumes of water. As shown in FIG. 3, fractions 65–100, indicated by shading, contained the polypeptide in highly purified form. The pH of the solution was brought to 2.5–2.7 with HCl and the polypeptides were recovered from solution by adsorption to alginic acid, elution with 0.2 M HCl and exchange of chloride for acetate, followed by lyophilization, as described for secretin. The lyophilized material weighed 18.5 mg.

ANALYTICAL RESULTS

The material obtained by countercurrent distribution showed only one band on polyacrylamide gel electrophoresis. Analysis for N-terminal amino acids by the phenylisothiocyanate method revealed only one such acid, histidine. This suggested that no further purification would be necessary for the determination of the structure of the polypeptide.

Aliquots of it were hydrolyzed with 6 M HCl and the hydrolysates subjected to quantitative amino acid analysis. The results indicate that the amino acid residue composition of the vasoactive intestinal polypeptide is $Ala_2Asx_4Arg_2Glx_1His_1Leu_2Lys_3$ $Met_1Phe_2Ser_3Thr_2Tyr_2$-$Val_3$. The complete sequence was described as above.

In order to determine the C-terminal amino acid, chymotrypsin digestion was conducted for 4 hours at 21° C. in 1% $NH_4HCO_3$ using 0.04 mg/ml enzyme and 2 mg/ml peptide. Half the quantity of the enzyme was added to the substrate at the beginning of the degradation, and the other half after 2 hours. In parallel with this, porcine vasoactive octacosapeptide was treated in exactly the same way. The digests were lyophilized, redissolved in half the original volume of water and heated for 6 minutes at 100° C. They were then lyophilized in 0.2 M acetic acid and submitted to high-voltage paper electrophoresis at pH 6.4. It was found that whereas, as expected, asparagine amide could be clearly identified among the chymotryptic degradation products of the porcine polypeptide, no trace of this could be seen among the fragments from the chicken material. Instead there was a fragment with higher cathodic mobility and giving a canary-yellow color with cadmium nin-hydrin reagent. This yellow color was indicative of either a glycyl or a threonyl peptide. Since the amino acid analysis had shown that the chicken, like the porcine, material lacked glycine, the chymotryptic degradation products of the chicken polypeptide were run in parallel, and mixed, with threonine amide. The results confirmed that the C-terminal amino acid in chicken vasoactive octacosapeptide is threonine amide.

The invention has been described herein by reference to certain preferred embodiments. However, as obvious variations thereon will become obvious to those skilled in the art the invention is not to be considered as limited thereto.

What is claimed is:

1. A method for the extraction and isolation of a vasoactive peptide from the intestines of fowl having the following general structure:
His-Ser-Asp-Ala-Val-Phe-Thr-Asp-Asn-Tyr-Ser-Arg-Phe-Arg-Lys-Gln-Met-Ala-Val-Lys-Lys-Tyr-Leu-Asn-Ser-Val-Leu-Thr-NH$_2$
which comprises extracting crude polypeptide concentrate from said intestines, purifying said crude concentrate at least by absorption with alginic acid, collecting fractions containing said crude concentrate, subjecting said crude concentrate to gel chromatography, collecting fractions thereof, subjecting the resultant fractions to extraction with a lower alkyl alcohol, recovering the product, subjecting the extracted product to ion-exchange chromatography, collecting fractions of the active product, and thereafter subjecting the further purified polypeptide to countercurrent distribution separation, and collecting the purified polypeptide.

2. The method of claim 1 including dissolving said crude peptide in a buffer at approximately pH 6–7 for said ion-exchange chromatography, and dissolving said crude peptide in an organic acid in said gel chromatography.

3. The method of claim 2 including dissolving said crude peptide in a buffer selected from sodium and ammonium carbonates, bicarbonates and phosphates and acid phosphates at a pH of 6.2–6.6 approximately, dissolving said crude peptide for said gel chromatography in an organic acid, said gel filter being selected from Sephadex and cellulose, using an alcohol-buffer, system to isolate said peptide.

4. The method of claim 3 including said buffers being Na$_2$HPO$_4$ for said ion-exchange, said organic acid with said gel chromatography being acetic acid and said countercurrent distribution separation system being 1-butanol and NH$_4$HCO$_3$, and said ion-exchange chromatography filter material being CMC.

5. The method of claim 1 including eluting the crude peptide with acid to obtain the fractions with peptide in the ion-exchange chromatographic step.

6. The method of claim 4 including maintaining the pH at 6.4 in said ion-exchange chromatography.

7. The novel purified polypeptide having the following structure:
His-Ser-Asp-Ala-Val-Phe-Thr-Asp-Asn-Tyr-Ser-Arg-Phe-Arg-Lys-Gln-Met-Ala-Val-Lys-Lys-Tyr-Leu-Asn-Ser-Val-Leu-Thr-NH$_2$.

8. A therapeutic composition comprising a therapeutically effective amount of the polypeptide of claim 7 and a physiologically acceptable carrier.

9. A composition according to claim 8 wherein the composition contains about 0.001 to 0.1 weight percent of polypeptide in the carrier.

10. A method for producing bronchodilation in animals and humans comprising administration by inhalation of a therapeutically effective amount of the polypeptide of claim 7.

* * * * *